United States Patent [19]

Stratbucker

[11] Patent Number: 5,678,545
[45] Date of Patent: Oct. 21, 1997

[54] ANISOTROPIC ADHESIVE MULTIPLE ELECTRODE SYSTEM, AND METHOD OF USE

[76] Inventor: Robert A. Stratbucker, 7125 Country Club Rd., Omaha, Nebr. 68152

[21] Appl. No.: 434,658

[22] Filed: May 4, 1995

[51] Int. Cl.⁶ .......................... A61B 5/0408; A61N 1/04
[52] U.S. Cl. .......................... 128/640; 128/641; 128/644; 607/148; 607/149; 607/152
[58] Field of Search .................... 128/639–641, 128/644; 607/148, 149, 152, 153; 606/32

[56] References Cited

U.S. PATENT DOCUMENTS

| | | |
|---|---|---|
| 3,612,061 | 10/1971 | Collins . |
| 4,121,575 | 10/1978 | Mills et al. . |
| 4,209,481 | 6/1980 | Kashiro et al. . |
| 4,328,814 | 5/1982 | Arkans . |
| 4,416,274 | 11/1983 | Jacobsen et al. ................ 607/153 |
| 4,465,074 | 8/1984 | Buchalter ....................... 128/639 |
| 4,524,087 | 6/1985 | Engel . |
| 4,583,549 | 4/1986 | Manoli . |
| 4,706,680 | 11/1987 | Keusch et al. . |
| 4,763,660 | 8/1988 | Kroll . |
| 4,778,635 | 10/1988 | Hechtman et al. . |
| 4,799,480 | 1/1989 | Abraham et al. . |
| 4,832,608 | 5/1989 | Kroll . |
| 4,848,353 | 7/1989 | Engel . |
| 4,919,648 | 4/1990 | Sibalis . |
| 4,921,475 | 5/1990 | Sibalis . |
| 4,955,381 | 9/1990 | Way et al. . |
| 4,957,109 | 9/1990 | Groeger . |
| 4,989,607 | 2/1991 | Keusch et al. . |
| 5,045,249 | 9/1991 | Jin et al. . |
| 5,080,099 | 1/1992 | Way et al. . |
| 5,124,107 | 6/1992 | Schmid . |
| 5,132,058 | 7/1992 | Suyama et al. . |
| 5,143,071 | 9/1992 | Keusch et al. . |
| 5,184,620 | 2/1993 | Cudahy et al. . |
| 5,191,886 | 3/1993 | Paeth et al. . |
| 5,224,479 | 7/1993 | Sekine . |
| 5,232,639 | 8/1993 | Reitz et al. . |
| 5,237,995 | 8/1993 | Cano ............................ 128/640 |
| 5,263,481 | 11/1993 | Axelgaard . |
| 5,265,579 | 11/1993 | Ferrari . |
| 5,289,822 | 3/1994 | Highe et al. . |
| 5,295,482 | 3/1994 | Clare et al. . |
| 5,331,959 | 7/1994 | Imran . |

OTHER PUBLICATIONS

Body Surface Laplacian Mapping of Cardiac Electrical Activity, He et al., J. Card, vol. 70, Dec. 1992.

Bioelectrical Higher–Order Derivative Mapping, He, IEEE 1994.

Body Surface Laplacian Mapping, Modeling and Clinical Approach, Parati et al, IEEE, 1994.

The limited View of The Surface Laplacian of body Surface Potentials, Oostendorp, IEEE, 1994.

(List continued on next page.)

*Primary Examiner*—Lee S. Cohen
*Attorney, Agent, or Firm*—James D. Welch

[57] ABSTRACT

A bioelectric interface is disclosed which provides a plurality of electrodes affixed to an adhesive sheet which demonstrates electrode isolating anisotropic electrical specific impedance properties simultaneous with isotropic pliability and adhesion mechanical properties. The bioelectric interface can be configured to provide electrodes positioned for use in, for instance, twelve lead (ECG) systems as well as in any other configuration. Groups of electrodes can be present in certain locational regions to allow single sized systems to fit to patients with various sized bodies. The electrodes can be of various physical shapes to allow not only direct signal measurement, but also to allow monitoring of high frequency content of signals and to allow enhanced resolution of a region from which measured signals originate. When present, extra electrodes in a group thereof can be used for purposes, such as cardiac pacing. In addition, the present invention bioelectric interface need not be removed to allow cardio-pulmonary-resuscitation or defibrillation to be performed, and it serves to preserve the relative spacial integrity of the positioning of the electrodes present during use.

27 Claims, 2 Drawing Sheets

OTHER PUBLICATIONS

On The Laplacian Inverse Electrocardiography, He, IEEE, 1994.

A 3-D Computer Simulation Study of Body Surface Laplacian Maps During Ventricular Activation, He et al, IEEE, 1994.

Disposable 12-Lead ECG Array & Interconnect Designed for ICU's, Biomedical Technology Information Service, vol. 17, No. 18, Oct. 1990.

Self-Adhesive Monitor/Defibrillation Pads Improve Prehospital Defibrillation Success, Stults et al, Annals Emers. Med. 1987.

ANISOTROPIC ADHESIVE MULTIPLE ELECTRODE SYSTEM, AND METHOD OF USE

TECHNICAL FIELD

The present invention relates to systems of electrodes for use in bioelectric interfacing. More particularly, the present invention is a system, and method of use, which utilizes anisotropic electrical specific impedance properties and essentially isotropic mechanical properties of certain adhesive sheets in conjunction with electrodes held in essentially constant spacial separation configurations to form a simple to use system suitable for interfacing electrocardiograph signals obtained at the location of a patient's chest.

BACKGROUND

Conventional medical analysis and therapy often involves use of a plurality of individual electrodes, each applied independently to an appropriate location on a patient's body by way of electrically conductive paste, and securing means such as a skin compatible adhesive. A relevant example of use is in the monitoring of Electrocardiogram (ECG) signals at left and right arm, and left Leg locations by independent electrodes in an Einthoven triangle.

Further, it is known to apply individual non-invasive precordial electrodes to a patient's chest to allow the acquiring of ECG data, to allow defibrillation of fibrillating hearts and to allow the pacing of arrested hearts and the like. A patent, U.S. Pat. No. 4,524,087 to Engel for instance describes a suitable such conductive electrode which is an adhesive, swellable, dermally-nonirritating, conformable, ionic hydropolymer biomedical electrode which is fabricated by a claimed process.

A problem which presents in the use of such independent electrodes, however, is that reliable, repeatable placement upon a patient's body is difficult. For instance, it is generally accepted that a majority of the errors encountered in acquiring ECG data is caused by improper electrode placement by medical technical staff.

Of relatively recent development are electrode pads which comprise a multiplicity of electrodes affixed to a flexible pad in an appropriate pattern for use in medical analysis and/or therapy. For instance, a patent to Manoli, U.S. Pat. No. 4,583,549 describes an ECG electrode pad in which six conductive discs are plated and etched on a flexible adhesive pad in a clinically conventional predetermined pattern effective for precordial ECG electrode placement. Reproducible attachment of said six electrodes to a patient's chest in the proper arrangement for use with standard ECG machines is thus made possible by a single application of an electrode pad of an appropriate size for use with a patient. However, it would seem that the Manoli system would require numerous sized electrode pads to accommodate patients of different sizes as the claims recite rather strict electrode placement criteria which are referenced with respect to a patient's body. A single electrode pad would not meet said requirements on patients of different sizes. A patent, U.S. Pat. No. 4,121,575 to Mills et al. describes a multiple electrode device for application to a Patient's chest, formed in stretchable non-conductive material having apertures in the V1–V6 positions. The capability for stretching the material is held to allow accurate positioning of Vi–V6 electrodes on patients of differing body size. A patent to Groeger et al., U.S. Pat. No. 4,957,109 describes an electrode assembly comprising right and left arm and leg leads, and precordial leads all affixed to a common structure. The arm and leg leads do not affix to a patient's chest during use. The Mills et al. and Groeger et al. systems do not serve to maintain a relatively fixed positioning of electrodes therein during use, and it is noted that movement between electrodes during use can cause noise generation in electrocardiography systems.

Patents to Way et al., U.S. Pat. Nos. 4,955,381 and 5,080,099 describe multiple conductive polymer pads containing electrodes for performing multiple electrical physiological functions from a set of electrodes with respect to a patient, at or about the same time, such as defibrillation, pacing and monitoring. Other patents which disclose multiple electrode assemblies are U.S. Pat. No. 4,328,814 to Arkans and U.S. Pat. No. 5,191,886 to Paeth et al. These patents each describe a plurality of electrodes configured in a physically seriesed configuration with conductive leads to various physically seriesed contacts, present at one end thereof. In addition, a patent to Collins, U.S. Pat. No. 3,612,061 describes a porous sheet of elastic material which supports an array of electrodes adapted to contact a wearer's skin, and U.S. Pat. No. 5,184,620 to Cudahy et al. describes an electrode pad system comprised of a multiplicity of electrodes which are utilized in defibrillation and pacing scenarios as directed by an on-line computer driven analysis and electrical energy application system, which system distributes electrical energy to appropriate sets of said multiplicity electrodes in response to patient needs.

Continuing, it is to be understood that particularly appropriate materials in which to form an electrode pad with a plurality of ECG monitoring electrodes present therein are hydropolymers. This is because hydropolymers can be pliable, self-adhesive and compatible with maintaining hydration of patient skin to which they affix during prolonged use. The pliable property makes hydropolymers exceptionally well suited for application to unpredictable irregularities of various patient's chests and the self adhesive property negates the need to apply adhesive material to affix the present invention to a patient during use. As well, the need to apply electrically conductive paste to electrically conducting areas of electrodes becomes unnecessary.

A patent, U.S. Pat. No. 5,331,959 to Imran, describes a low impedance dry conforming contact member in which are present rods or filaments which are cured into material such as a silicon-based material, such that when configured as an electrode provide impedance reducing projections which protrude into the pores of a patient's skin during use. Said rods or filaments reduce the need to use conductive paste.

Continuing, three patents to Keusch et al, U.S. Pat. Nos. 4,706,680, 4,989,607 and 5,143,071 describe hydrogels which are caused to be highly conductive by the inclusion of an essentially uniformly distributed active electrolyte therein. Said patents state that to form the hydrogels a polymeric mixture is caused to become cross-linked by exposure to radiant energy. This causes a gel-like solid to form which is sufficiently tacky and adhesive to adhere to subject's skin and which is substantially non-stringy and non-aggressive.

A patent to Highe et al., U.S. Pat. No. 5,289,822 describes an electrode formed of a dry-conductive material having an outer surface to be placed in contact with a patient's skin. A composition is deposited on at least a portion of the surface of the dry-electrode which comprises a plurality of water-containing vesicles. The purpose of said water-containing vesicles being to effect an immediate lowering of patient skin resistance upon the application of the electrode. It is stated that a period of approximately four minutes is otherwise required for moisture from a patient's skin to naturally occur at the electrode.

A patent to Schmid, U.S. Pat. No. 5,124,107 describes a process for manufacturing a body electrode which comprises one or more galvanically active sensors which are combined with a first layer capable of adhering to a patient's skin, on a body contact side thereof. A second covering or supporting layer is also present on the opposite side of the body electrode. The process for manufacture provides that the two layers are sequentially cast in a mold which provides intended shape and size. The procedure avoids manufacturing problems encountered where electrodes are stamped from a preformed sheet. A potential problem of using such an electrode as provided by the Schmid 107 patent is that it provides a laterally oriented conductive path between said galvanically active sensors through the first layer thereof. Electrically anisotropic conducting hydropolymers would be preferable.

Continuing, a patent to Suyama et al, U.S. Pat. No. 5,132,058 describes a process for producing an anisotropically electroconductive sheet having a plurality of electroconductive portions extending in the direction of the thickness of the sheet. Application of an anisotropic magnetic field is utilized to draw electroconductive particles into a molding material such that said electroconductive particles gather where said electromagentic field is applied. Another patent which describes a similar system to that achieved by practice of the Suyama et al. patent is U.S. Pat. No. 4,778,635 to Hechtman et al. A patent to Kashiro et al, U.S. Pat. No. 4,209,481 describes an anisotropically electroconductive sheet in which electroconductive wires are formed into patterned groupings, which patterned groupings are in turn formed into patterns. The wires are parallel in the direction of the sheet thickness, and spaced apart by nonelectroconductive elastomer. Another patent, U.S. Pat. No. 5,045,249 to Jin et al., describes electrical interconnections made by means of a layer or sheet medium comprising chains of magnetically aligned, electrically conductive particles in a nonconducting medium. End particles of chains protrude from a surface of the medium to effect electrical contact. A patent to Abraham et al., U.S. Pat. No. 4,779,480 describes an electrode for use with electrosurgical apparatus which provides capacitive coupling with the skin of a patient. The electrode includes a conductive plate connected to the electrosurgical apparatus with an insulating layer disposed in contact with the conductive plate and on the opposite face of the insulator there is provided conductive material in the form of a plurality of islands of conductive adhesive material which contact the skin of a patient during use. Another patent, U.S. Pat. No. 5,232,639 to Reitz et al. describes a process for forming articles with anisotropic void distributions therein.

It is also established that electrode configuration can be important in determining the accuracy of monitored signals. For instance, the use of a Bulls-eye shaped electrode, which comprises a central electrode surrounded by one or more annular ring electrodes, can provide signals which focus upon a specific region of a patient's heart, which focus is not available when a simple electrode geometry is utilized. As well, Bulls-eye shaped electrodes allow determination of derivatives of detected signals in use.

An article by He et al. titled "Body Surface Laplacian Mapping of Cardiac Electrical Activity" published in The American J. of Cardiology, Vol. 70, Dec. 15, 1992 describes the use of Bulls-eye shaped electrodes to map derivatives of cardiogenic signals.

Patents which describe unusual geometrical electrode configurations are, for instance, a patent to Clare et al., U.S. Pat. No. 5,295,482 which discloses a large surface area electrode in which a central portion is surrounded by two surrounding ring portions, said central and two surrounding ring portions being separated from one another by annular regions. This patent states that during use current density is found to be greater at the outer edge of an electrode than if it is at a more centrally located location. The purpose of the described system is disclosed as being to effect a more uniform distribution of current density over the effective large surface area of the disclosed electrode during use, by providing multiple "outer-edge" providing portions.

Even in view of the above cited literature, need remains for a convenient to utilize body electrode, suitable for application to patients of differing body sizes, which body electrode is preferably made of an electrically anisotropic conducting self adhesive material, and which body electrode provides electrodes of a geometry appropriate for optimizing electrical contact to a patient and for providing accurate monitored signals therefrom during use.

DISCLOSURE OF THE INVENTION

To facilitate disclosure of the present invention in this Disclosure, a relevant example of use therefore will be provided. Said example concerns the practice of electrocardiography (ECG) wherein a number of electrical signals which are diagnostic of coronary function are acquired via electrodes placed upon a patient's body. As regards this use, patient contacting electrodes can be spacially oriented in Einthoven triangle, Frank, McFee, Schmidt and twelve lead configurations etc., and in array patterns for use in mapping, etc. While twelve lead systems will be primarily further discussed herein, said exemplary use is not to be interpreted to constitute a limitation in electrode arrangement of the present invention.

As demonstrated in the Background Section of this Disclosure, multiple electrode systems are not unknown. However, said known systems do not provide all electrodes for use in an (ECG) system, for instance, conveniently positioned on a bioelectric interface which can, for instance, be easily, accurately and repeatably applied to a patient's chest in a desired location. Considering a twelve lead (ECG) system, conventional practice requires that electrodes be placed on a patient's Right (RA) and Left (LA) arms and Left leg (LL), and that six precordial electrodes (V1, V2, V3, V4, V5, and V6), be placed upon the patient's chest. The locations of the V1–V6 electrodes are:

V1—in the fourth intercostal space at the right sternal border;

V2—in the fourth intercostal space at the left sternal border;

V4—in the fourth intercostal space at the mid-clavicular line;

V3—midway between the V2 and V4 electrodes;

V5—in the fifth intercostal space at the anterior auxiliary line;

V6—in the fifth intercostal space in the mid-auxiliary line.

No known reference, however, suggests that arm and leg equivalent electrodes should be placed at chest locations relatively near the precordial electrodes. The present invention teaches that said arm and leg equivalent electrodes are to be so placed. The location of said arm and leg equivalent electrodes is best understood by reference to the Drawings which are discussed in the Detailed Description of this Disclosure, however, verbally their positioning can be;

Right Arm—in the second intercostal space to the right of the sternam;

Left Arm—in the second intercostal space at the mid-auxiliary line; and

Left Leg—in the inferior costal margin at the mid-clavicular line.

In addition, the present invention teaches the optional use of multiple element electrodes, (eg. "Bulls-eye" shaped electrodes), for instance, in a multiple element electrode system. Use of Button electrodes is conventional, and in use each such Button electrode serves to measure an electrical signal between it and a common or reference electrode. That is, all present Button electrodes are referred to one common electrode. When multiple element (eg. Bulls-eye), electrodes are utilized, however, signals are generated between two components of a single electrode. Continuing, a Bulls-eye shaped electrode is configured like a target. That is, typically a Button electrode will be centrally located within an outer annular shaped ring electrode. The benefits provided by such multi-element electrodes are the ability to achieve greater resolution of signals generated in a specific area of a patient's heart, and it is noted, that signals measured are representative of the derivatives of electrical signal activity produced by a patient's heart. That is, the signal provided between a Button and First Annular Ring is proportional to a first derivative of a signal generated by a patient's heart. Additional annular ring electrodes can also be present and signals measured thereby are proportional to higher order derivatives. Use of "Bulls-eye" electrode geometry then allows investigation of High Frequency aspects of electrical activity generated by a patient's heart. It is noted that a limitation is associated with the use of Bulls-eye electrodes in that the smaller dimensioned they become, although enabling increased resolution and investigation of electrical signals generated in smaller regions in a heart, the smaller the magnitude of signal they provide. In a multiple electrode setting then, where relative motion between electrodes can create electrical noise, it then becomes increasingly important to prevent relative motion between electrodes, and components of Bulls-eye electrodes, when Bulls-eye electrodes are present. (Note, it is emphasized that it is possible to achieve a result similar to that provided by "Bulls-eye" electrodes with other multiple element electrodes, and for the purposes of this Disclosure any functionally similar electrode is to be considered as included by the terminology "Bulls-eye" whether a closed annular ring is present or not).

With the forgoing in mind, it is then to be appreciated that the system of the present invention is a bioelectric interface comprised of a plurality of electrodes which are affixed to an adhesive sheet in a desired spacially separated pattern, such that in use said electrodes are essentially fixed in location with respect to one another. It is noted that fixing said relative position between electrodes serves to reduce electrical noise which can be generated when, in use, electrodes move with respect to one another. Again, it is to be understood that the electrodes can be of Button or Bulls-eye, (or other), geometry as well.

Continuing, the adhesive sheet of the present invention has the properties of simultaneously demonstrating essentially electrically anisotropic properties but mechanically, (eg. pliability and adhesion), isotropic properties. That is, the specific impedance across the sheet is significantly different from that laterally along said sheet, but the mechanical properties such as adhesion and pliability are essentially consistent. (Note, the term "specific impedance" is used to refer to the bulk property of the adhesive, rather than properties resulting from dimensions of elements fabricated therefrom). In the preferred embodiment, the adhesive sheet is a hydropolymer which demonstrates a tackyness on a patient skin contact side thereof. Hydropolymers are particularly applicable in realization of the present invention as they are electrically conductive, relatively non-irritating to patient skin, and they demonstrate excellent adhesive qualities. Commercially available hydropolymer sheets with isotropic electrical properties, are available from Promeon of Boston, Mass. under the product designation RG-60 Series Hydrogels. Lec-Tec of Minneapolis, Minn. also markets hydrogels. The present invention provides that such adhesive hydropolymer sheet material can be utilized, if "slits" are entered thereto at appropriate locations to effect electrical anisotropicity between electrodes present at various laterally offset locations. It is noted that hydropolymer sheets do not typically demonstrate a rigidity sufficient to maintain a spacially stable relationship between electrodes affixed thereto, but particularly when slits are formed therein, the present invention requires that a carrier matrix be present to which electrodes and said adhesive sheet attach. That is, the system of the present invention will then comprise a carrier matrix to which are attached, at desired spacially offset locations, electrodes, over which said hydropolymer is placed so that said electrodes are sandwiched between said carrier matrix and hydropolymer. At locations between the various electrodes said "slits" are then caused to be present by a mechanical process. It is noted that in practice said slits are typically not of a degree to provide complete discontinuity between various regions of the resulting hydropolymer. This configuration has been found to provide an essentially anisotropic specific impedance system. The background Section also identifies various electrically anisotropic adhesive materials. The present invention, in addition, teaches that an essentially electrically anisotropic adhesive sheet can be provided by an electrically nonconducting "Scrim" material comprising a number of channels therethrough, which channels are caused to be filled with an electrically conductive adhesive material, (preferably a hydropolymer), such that "island channels" of conductive material exist across the resultant sheet, but such that electrically nonconductive scrim exists between laterally oriented islands of conductive material.

Continuing, the present invention, in its preferred embodiment, teaches that one size of multiple electrode bioelectrical interface should be sufficient for use with all patients, regardless of body size. The present invention teaches that to accomplish placement of electrodes, such as defined infra for twelve lead systems, on patients bodies of various size, that groups of electrodes should be available in the region of, for instance, the forth intercostal space at the right sternal border, (ie. the location for a V1 lead). In use then, regardless of a patient body size, one electrode in a group of electrodes in the region of the forth intercostal space at the right sternal border, will provide an optimum result. Which electrode in a group of electrodes provides said optimum result, will of course be patient specific. Prior art has failed to recognize the need to provide a group of electrodes in the region of a specific location so that a user can select an optimumly placed electrode for a specific patient.

It is also noted that as the relative spacial separation of the various electrodes is essentially fixed by the present invention, and that their position on a patient's body is secured by the adhesive sheet, it is possible to conduct activities such as coronary-pulmonary-resuscitation (CPR) on a patient to which the present invention is applied, without removal thereof. Such is essentially impossible where individual leads are utilized in an (ECG) system. As well, the present invention teaches that the means for making electrical contact to the electrodes should be available on the outer surface of the bioelectrical interface. For instance, snaps might be provided so that leads from an (ECG) system can easily attach thereto. Being electrically conductive, it is possible, in an emergency, to apply defibrilation paddles to said means for making electrical contact without removing the present invention bioelectrical interface from the patient. Because the present invention is firmly affixed to a patient, the defibrilation shock will be transmitted to the patient with little attenuation. One can also utilize electrodes in the present invention bioelectric interface for heart pacing, and perhaps even electrosurgery.

The present invention will be better understood by reference to the Detailed Description Section in conjunction with the accompanying Drawings.

BRIEF DESCRIPTION OF THE DRAWINGS

FIG. 2 shows a view of a two electrode bioelectric interface with a common adhesive sheet applied thereto, in which common adhesive sheet is present an electrically anisotropic property causing slit present between.

DETAILED DESCRIPTION

Figure 1A:
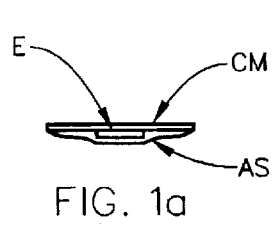
FIG. 1a shows a side elevational view of a bioelectric interface showing an electrode "sandwiched" by an adhesive sheet and a carrier matrix.

Turning now to the Drawings, there is shown in FIG. 1a a side elevational cross sectional view of a single electrode (E) in a bioelectric interface (1) system comprising a carrier matrix (CM) and an adhesive sheet (AS). Note that the electrode (E) is "sandwiched" between the carrier matrix (CM) and adhesive sheet (AS). This is a typical arrangement, but where an adhesive sheet can provide sufficient spacial positioning integrity it is to be understood that the carrier matrix can become unnecessary.

Figure 1B:
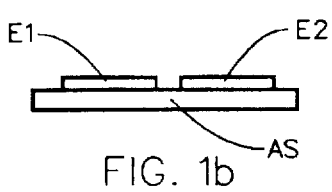
FIG. 1b a generic combination of an electrically anisotropic adhesive with multiple electrodes placed thereupon.

FIG. 1b shows a generic embodiment of the present invention. Note that two electrodes (E1) and (E2) are present atop an electrically anisotropic adhesive sheet (AS) such that a bioelectric interface comprising an adhesive sheet in functional combination with at least two spacially separated electrodes is formed. The adhesive sheet (AS) is to be understood to simultaneously present with essentially anisotropic specific impedance properties and essentially isotropic mechanical pliability and adhesion properties. Said electrodes (E1) and (E2) are affixed to said adhesive sheet in a manner such that their relative positions with respect to one another are essentially fixed, and such that the specific impedance from each electrode directly through said adhesive sheet, is less than that between any said electrodes through said adhesive sheet (AS).

Figure 2:
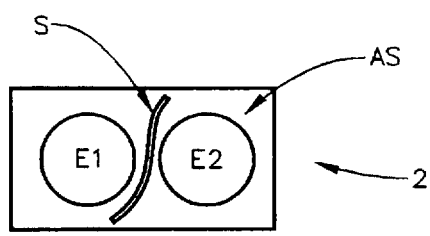

FIG. 2 shows a bioelectric interface system (2) comprised of two electrodes (E1) and (E2) looking from the surface thereof upon which is present an adhesive sheet (AS), (ie. that surface which will contact a patient's skin in practice). Note that a "slit" (S) is shown as present between said electrodes (E1) and (E2). In the case where the adhesive sheet is made of an electrically isotropic material, (eg. commercially available hydropolymers in sheet form for instance), it has been found that providing a slit (S) between two electrodes (E1) and (E2) effects essentially electrically anisotropic properties thereto. That is, a lower specific impedance will be measured from an electrode through the adhesive sheet than between two electrodes. In the case that an adhesive sheet provides such anisotropic electrical specific impedance properties, said slit (S) typically becomes unnecessary. It is noted that the reason the adhesive sheet should provide anisotropic electrical properties is that in an (ECG) setting, for instance, if the adhesive sheet is electrically isotropic, signals which should be present in one electrode in a bioelectric interface, will to some extent be present in other electrodes as well, as a result of lateral current flow through said adhesive sheet. This effect, as far as the inventor knows, has not been previously addressed, and many prior multiple electrode systems therefore, enter an artifact to (ECG) data as a result. As well, adhesive sheet electrical anisotropicity allows use of higher resolution electrode geometry, (discussed supra) because lateral current flow is limited.

It will be noted that the adhesive sheet (AS) in FIG. 2 is not completely bisected by the slit (S). This is a preferred practice, because complete electrode isolation is not always optimum. For instance, in (ECG) system settings it is common to inject a noise compensating signal to a Right Leg electrode via a driver circuit, which signal is to be imposed upon all electrodes. This practice is well known by practitioners in the (ECG) field, with noise compensating current flow normally being through a patient's skin, but it has been found that allowing some electrical path through the adhesive sheet does not noticeably degrade acquired (ECG) data. With that thought in mind it is noted that a goal of the present invention is to provide a very firm affixation to a patient such that spacial separation between electrodes is maintained constant and such that good electrical contact between electrodes and a patient's skin is effected, via said adhesive sheet. Hence, the more surface area of the present invention bioelectric interface upon which the adhesive sheet remains present, the better.

Figure 3A:
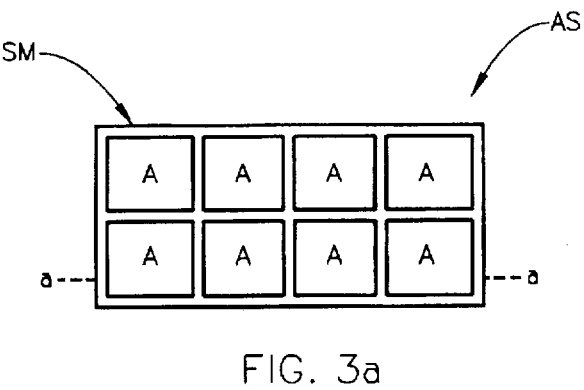
FIGS. 3a and 3b show top and side elevation views respectively of a novel electrically anisotropic adhesive sheet.
Figure 3B:
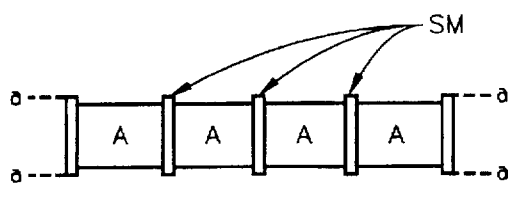

FIGS. 3a and 3b show a present invention system for providing electrically anisotropic specific impedance in an "adhesive sheet". Shown is an electrically nonconductive "Scrim" (SM) present in a form which provides numerous channel regions, said channel regions being filled with electrically isotropic conductive adhesive material (A).

Figure 4A:
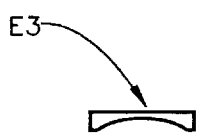
FIGS. 4a and 4b show various electrode designs.
Figure 4B:
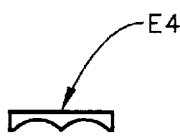
Figure 4C:
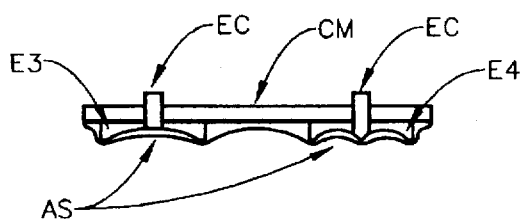
FIG. 4c shows the electrodes of FIGS. 4a and 4b sandwiched between a carrier matrix and an adhesive sheet.

Turning now to FIGS. 4a and 4b, there are shown preferred shapes (E3) and (E4) for electrodes. Note that there are regions of said electrodes which will tend to project into an adhesive sheet (AS) placed in contact therewith. The effect of said projection is to provide a thinning of the adhesive sheet (AS) and effect an electrically anisotropic character to the adhesive sheet (AS) as viewed in cross section. That is, electrical specific impedance from an electrode (E3) or (E4) through said adhesive sheet (AS) will be caused to be less than that between electrodes (E3) and (E4)

through said adhesive sheet (AS), because of a thinning effect at the projecting edges of said electrodes. FIG. 4c demonstrates the adhesive sheet (AS) thinning effect. Any electrode shape effecting a similar effect is to be considered equivalent. FIG. 4c also shows the presence of external device electrical connector means (EC).

Figure 5:
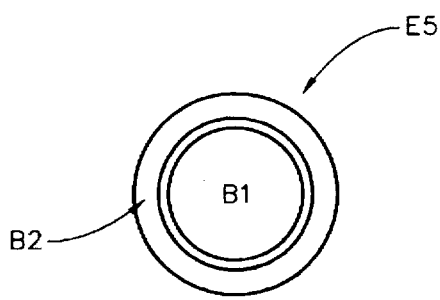
FIG. 5 shows a multi-element electrode configured in a Bulls-eye pattern.

FIG. 5 shows an example of a multi-element electrode (E5) with a "Bulls-eye" geometry. As described in the Disclosure of the Invention Section of herein, use of said multiple element electrodes allows investigation of high frequency components in (ECG) signals, and allows better spacial resolution of the sources of monitored (ECG) signals. (It is to be understood that the "Bulls-eye" shape is an example of a multi-element electrode, and that any functionally similar multi-element electrode configuration is to be considered as included within the term "Bulls-eye"). The underlying distinction between multi-element electrodes and single element electrodes being that multiple single element electrodes typically utilize a common electrode as a reference, whereas multi-element electrodes provide their own reference point. It will be appreciated that electrical anisotropicity can become very important in view of the higher resolution capability of "Bulls-eye" electrodes, when signals are being monitored from closely positioned points of, for instance a human heart muscle. That is, greater resolution capability is of no consequence if the signal reaching a sensing electrode is effected by lateral current flow through an attached adhesive sheet, which signal was originated by a distal source.

Figure 6:
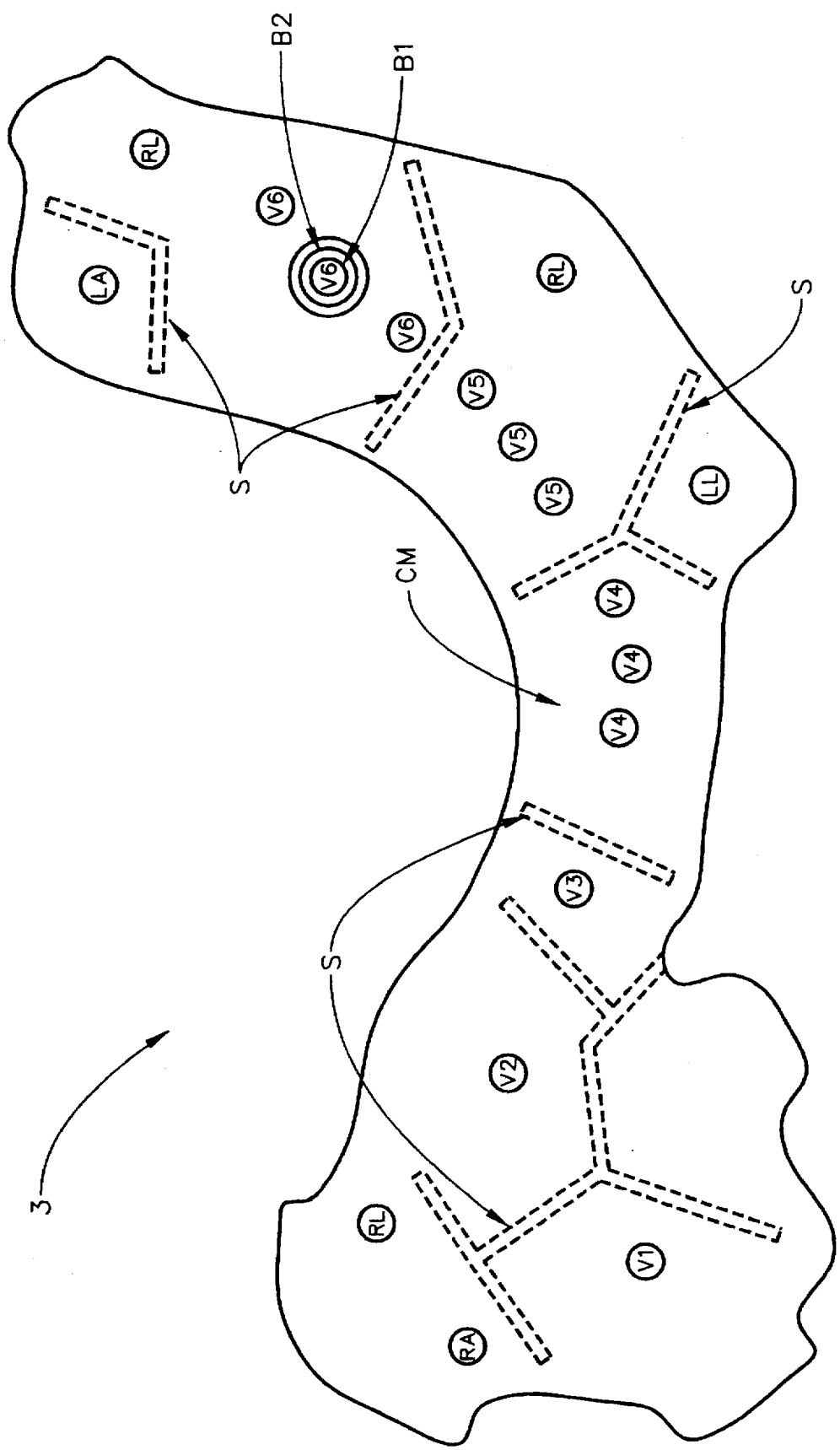
FIG. 6 shows a "life size" bioelectric interface configured for use with a twelve lead (ECG) system. Shown are groups of electrodes which serve to allow a "one-size-fits-all" result. Also shown is an exemplary presence of a multi-element Bulls-eye electrode, and the presence of "slits" in an adhesive sheet to effect electrical anisotropic properties therein.

Turning now to FIG. 6 there is shown an "actual size" typical present invention bioelectrical interface system (3) with electrodes present therein and appropriately spacially distributed and positioned for use with a twelve lead (ECG) system. FIG. 6 shows the surface of the present invention bioelectrical interface (3) opposite to that upon which is present an adhesive sheet which contacts a patient's skin in use. In use the bioelectrical interface system (3) will typically be placed upon a patient's chest with the various V1-V6 electrodes, and electrode groups, placed as follows:

electrode V1—in the region of the fourth intercostal space at the right sternal border.

electrode V2—in the region of the fourth intercostal space at the left sternal border;

electrode V4—in the region of the fourth intercostal space at the mid-clavicular line;

electrode V3—in the region half way between electrodes V2 and V4;

electrode V5—in the region of the fifth intercostal space at the anterior axillary line; and electrode V6—in the region of the fifth intercostal space at the mid-axillary line.

Note that electrodes V4, V5 and V6 are each shown as a group of electrodes. The present invention provides for any of the electrodes V1–V6 and any other electrodes which might be present, to be present as a group thereof. The reason for this is that the present invention bioelectrical interface is truely a "single size fits all system". That is, even though patient's bodies vary greatly one to another, the present invention can be applied to essentially any non-deformed patient and an electrode within a group of electrodes in the region of an appropriate location will be found to be properly positioned for use, within an error which exists even if individual electrodes are utilized, (said error originating from improper application of a single electrode). It is emphasized that while only V4, V5 and V6 precordial electrodes are shown as groups of electrodes in FIG. 6, any electrode shown, or any other configuration of electrodes utilized can be present as a group of electrodes as necessary to effect the "one-size-fits-all" aspect of the present invention bioelectric interface system.

Shown also in FIG. 6 are the Right Arm (RA), Left Leg (LL) and Left Arm (LA) electrodes, positioned as appropriate for use in an Einthoven triangle configuration, and for use as Right Arm (RA), Left Leg (LL) and Left Arm (LA) equivalent electrodes in the present invention bioelectrical interface. Said electrodes are positioned as: p1 electrode (RA)—in the region of the second intercostal space to the right of the sternum;

electrode (LL)—in the region of the inferior costal margin at the mid-clavicular line; and electrode (LA)—in the region of the second intercostal space at the mid-axillary line.

(Note, additional electrodes designated Right Leg (RL) are also present. As alluded to above, the Right Leg (RL) electrode in (ECG) settings is typically utilized to inject an out-of-phase noise compensating signal, which is equally applicable to many electrodes. It has been determined that said noise compensating signal can be injected at any essentially any location on the present invention bioelectrical interface without degradation of the results).

Also note that slits (S) in an electrically isotropic adhesive sheet are shown in broken lines. As viewed, said adhesive sheet would be present on a lower surface of the shown present invention bioelectric interface (3), hence are shown as viewed through the adhesive sheet and indicated carrier matrix (CM). Said slits (S) will be less necessary, and probably unnecessary, where an adhesive sheet constructed from an inherrantly electrically anisotropic material, such as demonstrated by FIGS. 3a and 3b, is utilized. In such systems the scrim (SM) can provide structural integrity, while the present electrically conductive adhesive can provide sufficient adhesive contact and electrical conductivity.

Also note that FIG. 6 shows one of the V6 electrodes as a "Bulls-eye" electrode with a central Button (B1) and outer annular ring (B2) present. Again, this is demonstrative, and in effect all electrodes could be of a multi-element construction. (Note than the central Button (B1) can still serve as a standard Button electrode). In use, one could also interconnect the V6 (B1) and (B2) elements, or all the electrodes in a group. For instance, suppose it became necessary to defibrillate a patient while a present invention bioelectric interface is in place. Conventional practice would require removal of any such electrode providing system. However, where the present invention bioelectric interface (3) is present, defibrillation paddle could be positioned to effectively form a single electrode from electrodes in the V4, V5 and V6 groups. (Note said defibrillation paddle could contact external contact means such as shown in FIG. 4c). The opposite defibrillation paddle could likewise be simultaneously applied to the V1, V2 and V3 electrodes, (or group of electrodes should alternatives be present at V1, V2 and V3 electrode locations).

It is to be noted that FIG. 6 shows electrodes V1, V2 and V6 as single electrodes and electrodes V4, V5 and V6 are shown as groups thereof. In practice, application of the present invention bioelectric interface system to a patient's body will proceed in a manner that typically assures appropriate positioning of electrodes V1, V2 and V3 on a patient's chest. The remaining electrodes will then make contact with the patient's body based upon the size and shape of the bioelectrical interface (3), which for any specific electrode might or might not be at the generally accepted locations recited infra. Where a group of electrodes is present, however, one of the electrodes in the group will be found to be appropriately positioned. It is also noted that where groups of electrodes are present, unused electrodes in a group can be utilized as, for instance, electrodes to effect cardiac pacing. As well, if one electrode in a group becomes inoperable, another can be substituted and still allow acquisition of reasonable (ECG) data.

Again, FIG. 6 provides a nonlimiting example of a bioelectrical interface of the present invention. The present invention is, however, in the combination of the various elements thereof, as well as in electrode positioning in a specific version.

As a general comment, it is to be appreciated that the present invention bioelectrode system provides a means by which many electrodes can be applied to a patient by a simple, error limiting procedure. As it is generally accepted that improper application of electrodes is the most common reason for faulted (ECG) data acquisition, this is significant. As well, the present invention bioelectrical interface provides a rather significant body contact surface area, said surface area being essentially covered with an adhesive material. This serves to ensure that electrodes, once applied to a patient, will not vary from the positions in which they are applied, and should not vary with respect to one another. It is known that relative motion between electrodes accounts for production of noise in acquired (ECG) data. The present invention greatly limits problems associated with noise generated by this effect. In fact, it is generally possibly to perform cardio-pulmonary-resuscitation on patients wearing the present invention bio-electric interface while continuing to acquire (ECG) data. It is also mentioned that when the adhesive sheet is a hydropolymer, patient discomfort is minimized, and moisture resulting from sweating etc. actually serves to improve the adhesion properties.

While not shown, it is possible to form arrays of electrodes in a present invention bioelectrical interface, for use in cardiac mapping. In such arrays, electrode arrangement is typically rectangular with, for instance, sixteen, twenty-four, thirty-six etc. electrodes present. The electrodes present can be of Button or Bulls-eye geometry, or, in other embodiments of the present invention, can be of any functional geometrical shape It is also noted that it is possible to affix alternative embodiments of the present invention bioelectrical interface to the back of a patient as well as to the chest thereof.

Having hereby disclosed the subject matter of the present invention, it should be obvious that many modifications, substitutions, and variations of the present teachings are possible in view of the teachings. It is therefore to be understood that the present invention may be practiced other than as specifically described, and should be limited in breadth and scope only by the claims.

I claim:

1. A bioelectric interface comprising an adhesive sheet in functional combination with at least two spacially separated electrodes, which adhesive sheet simultaneously presents with essentially anisotropic specific impedance properties and essentially isotropic mechanical pliability and adhesion properties, said electrodes being affixed to said adhesive sheet in a manner such that their relative positions with respect to one another are essentially fixed, and such that the specific impedance from each said electrode directly through said adhesive sheet, is less than that between any said electrodes through said adhesive sheet, said electrical anisotropic specific impedance properties of said adhesive sheet being the result of a slit or slits therein, which slit or slits is/are positioned between electrodes.

2. A bioelectric interface as in claim 1, in which the adhesive sheet is comprised of electrically conductive polymer.

3. A bioelectric interface as in claim 2, in which the electrically conductive polymer is hydrophillic, and thereby particularly well suited for application to human skin.

4. A bioelectric interface as in claim 1, in which the electrodes are each of a construction such that contact with the adhesive sheet is essentially continuous over the dimension of each said electrode.

5. A bioelectric interface as in claim 1, in which at least one of said electrodes is of a multiple-piece construction such that each of said multiple pieces contacts the adhesive sheet independently and essentially continuously over the dimension of each said multiple pieces.

6. A bioelectric interface as in claim 5 in which the multipiece construction configures a Bulls-eye pattern.

7. A bioelectric interface as in claim 6, in which there are present a multiplicity of electrodes configured in an essentially rectangular shaped matrix such that in use said bioelectric interface is affixed to one of the group consisting of a patient's chest and back, said bioelectric interface being appropriate for use in electrocardiographic mapping.

8. A bioelectric interface as in claim 1, which further comprises a tarrier matrix affixed thereto so as to sandwich said electrodes between said carrier matrix and said adhesive sheet, the purpose being to improve the integrity of the spacial separation between said electrodes.

9. A bioelectric interface as in claim 1, which further comprises means for electrically connecting said electrodes to external devices.

10. A bioelectric interface as in claim 1, in which there are present a multiplicity of electrodes configured in an essentially rectangular shaped matrix such that in use said bioelectric interface is affixed to one of the group consisting of a patient's chest and back, said bioelectric interface being appropriate for use in electrocardiographic mapping.

11. A bioelectric interface comprising an adhesive sheet in functional combination with at least two spacially separated groups of electrode(s), at least one of which spacially separated group of electrode(s), can consist of more than one electrode, which adhesive sheet simultaneously presents with essentially anisotropic specific impedance properties and essentially isotropic pliability and adhesion mechanical properties, electrodes in said spacially separated groups of electrode(s) being affixed to said adhesive sheet in a manner such the relative positions of electrodes present with respect to one another are essentially fixed, and such that the specific impedance from each electrode in said groups of spacially separated electrodes(s) directly through said adhesive sheet, is less than that between any two electrodes in different spacially separated groups of electrodes through said adhesive sheet, said electrical anisotropic specific impedance properties of said adhesive sheet being the result of a slit or slits therein, which slit or slits is/are positioned between groups of electrodes.

12. A bioelectric interface as in claim 11, in which the adhesive sheet is comprised of electrically conductive polymer.

13. A bioelectric interface as in claim 12, in which the electrically conductive polymer is hydrophillic, and thereby particularly well suited for application to human skin.

14. A bioelectric interface as in claim 13, which further comprises three additional groups of electrode(s) which are configured and sized so as to place said additional three groups of electrodes in an essentially congruent Einthoven triangle equivalent Left Arm, Right Arm, Left Leg pattern, such that in use all said groups of electrodes contact a patient's chest.

15. A bioelectric interface as in claim 11, in which the electrodes in the groups of electrode(s) are each of a construction such that contact with the adhesive sheet is essentially continuous over the dimension of each said electrode.

16. A bioelectric interface as in claim 11, in which at least one of said electrodes in said groups of electrode(s) is of a multiple-piece construction such that each of said multiple pieces contacts the adhesive sheet independently and essentially continuously over the dimension of each said multiple pieces.

17. A bioelectric interface as in claim 16, in which the multipiece construction configures a Bulls-eye pattern.

18. A bioelectric interface as in claim 11, which further comprises a carrier matrix affixed thereto so as to sandwich said electrodes in said groups of electrode(s) between said carrier matrix and said adhesive sheet, the purpose being to improve the integrity of the spacial separation between said electrodes.

19. A bioelectric interface as in claim 11, which further comprises means for electrically connecting said electrodes in said groups of electrode(s) to external devices.

20. A bioelectric interface as in claim 11, in which the number of groups of electrode(s) is three, said bioelectric interface being configured and sized so as to place said three groups of electrodes in an essentially congruent Einthoven triangle equivalent Left Arm, Right Arm, Left Leg pattern, such that in use all said groups of electrodes contact a patient's chest.

21. A bioelectric interface as in claim 11, in which the number of groups of electrode(s) is nine, said nine groups of electrode(s) being configured in an I, II, III, V1, V2, V3, V4, V5, V6 twelve lead electrocardiogram system electrode pattern, such that said nine groups of electrode(s) are positioned on a patient's chest during use as follows:

electrode group I in the region of the second intercostal space to the right of the sternum;

electrode group II in the region of the second intercostal space at the mid-axillary line;

electrode group III in the region of the inferior costal margin in the mid-clavicular line;

electrode group V1 in the region of the fourth intercostal space at the right sternal border;

electrode group V2 in the region of the fourth intercostal space at the left sternal border;

electrode group V4 in the region of the fifth intercostal space at the mid-clavicular line;

electrode group V3 in the region of the midpoint between electrode groups V2 and V4;

electrode group V5 in the region of the fifth intercostal space in the anterior axillary line; and electrode group V6 in the region of the fifth intercostal space in the mid-axillary line;

such that during use one electrode from each group of electrode(s) will be found to be more appropriately situated for a specific patient depending upon the patient's body size.

22. A method of acquiring electrocardiographic data comprising the steps of:

a. providing a bioelectric interface comprising at least two spacially separated groups of electrode(s), at least one of which spacially separated group of electrode(s) can consist of more than one electrode, which adhesive sheet presents with essentially anisotropic specific impedance properties but essentially isotropic mechanical properties, said spacially separated groups of electrode(s) being affixed to said adhesive sheet in a manner such that their relative positions with respect to one another remain essentially fixed, and such that the specific impedance from each electrode in said groups of spacially separated electrode(s) directly through said adhesive sheet, is less than that between any two electrodes in different spacially separated groups of electrodes through said adhesive sheet, said electrical anisotropic specific impedance properties of said adhesive sheet being the result of a slit or slits therein, which slit or slits is/are positioned between groups of electrodes, in which bioelectric interface the number of groups of electrode(s) is nine, said nine groups of electrode(s) being configured in an I, II, III, V1, V2, V3, V4, V5, V6 twelve lead electrocardiogram system electrode pattern, such that said nine groups of electrode(s) are positioned on a patient's chest during use as follows:

electrode group I in the region of the second intercostal space to the right of the sternum;

electrode group II in the region of the second intercostal space at the mid-axillary line;

electrode group III in the region of the inferior costal margin in the mid-clavicular line;

electrode group V1 in the region of the fourth intercostal space at the right sternal border;

electrode group V2 in the region of the fourth intercostal space at the left sternal border;

electrode group V4 in the region of the fifth intercostal space at the mid-clavicular line;

electrode group V3 in the region of the midpoint between electrode groups V2 and V4;

electrode group V5 in the region of the fifth intercostal space in the anterior axillary line; and electrode group V6 in the region of the fifth intercostal space in the mid-axillary line;

such that during use one electrode from each group of electrode(s) will be found to be more appropriately situated for a specific patient depending upon the patient's body size;

b. affixing said bioelectric interface to a patient and causing the electrodes therein to be electrically attached to an electrocardiographic system such that electrocardiographic data is obtained.

23. A method of acquiring electrocardiographic data as in claim 22, which further comprises the simultaneous step of performing a procedure selected from the group consisting of;

a. cardio-pulmonary resuscitation b. cardiac defibrillation;

c. cardiac pacing; and d. electro surgery;

on said patient without removing said bioelectric interface.

24. A method of acquiring electrocardiographic data as in claim 22, which further comprises the simultaneous step of causing at least some some of said electrodes to have a multiple component configuration.

25. A method of performing cardiac mapping comprising the steps of:

a. providing a bioelectric interface comprising an adhesive sheet in functional combination with at least two spacially separated electrodes, which adhesive sheet presents with essentially anisotropic specific impedance properties but essentially isotropic mechanical properties, said electrodes being affixed to said adhesive sheet in a manner such that their relative positions with respect to one another remain essentially fixed, and such that the specific impedance from each said electrode directly through said adhesive sheet, is less than that between any said electrodes through said adhesive sheet, said electrical anisotropic specific impedance properties of said adhesive sheet being the result of a slit or slits therein, which slit or slits is/are positioned between electrodes, in which bioelectric interface there are present a multiplicity of electrodes configured in an essentially rectangular shaped matrix such that in use said bioelectric interface is affixed to one of the group consisting of a patient's chest and back, said bioelectric interface being appropriate for use in electrocardiographic mapping;

b. affixing said bioelectric interface to a patient on one of the elements in the group consisting of a patient's chest and back, and causing said electrodes to be connected to an electrocardiograph mapping system.

26. A method of acquiring electrocardiographic data as in claim 25, which further comprises the simultaneous step of performing a procedure selected from the group consisting of;

a. cardio-pulmonary resuscitation b. cardiac defibrillation;

c. cardiac pacing; and d. electro surgery.

27. A method of acquiring electrocardiographic data as in claim 25, which further comprises the simultaneous step of causing at least some of said electrodes to have a multiple component configuration.

* * * * *